(12) United States Patent
Yamazaki et al.

(10) Patent No.: US 9,700,205 B2
(45) Date of Patent: Jul. 11, 2017

(54) OPHTHALMOLOGIC APPARATUS

(71) Applicant: CANON KABUSHIKI KAISHA, Tokyo (JP)

(72) Inventors: Shoichi Yamazaki, Yokohama (JP); Kazuhiro Matsumoto, Yokohama (JP); Nobuhiro Tomatsu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 10 days.

(21) Appl. No.: 14/840,181

(22) Filed: Aug. 31, 2015

(65) Prior Publication Data

US 2016/0066784 A1    Mar. 10, 2016

(30) Foreign Application Priority Data

Sep. 8, 2014  (JP) ................. 2014-182290

(51) Int. Cl.
| | |
|---|---|
| *A61B 3/14* | (2006.01) |
| *A61B 3/12* | (2006.01) |
| *A61B 3/00* | (2006.01) |
| *A61B 3/117* | (2006.01) |
| *G02B 27/14* | (2006.01) |
| *G02B 27/00* | (2006.01) |

(52) U.S. Cl.
CPC ............. *A61B 3/12* (2013.01); *A61B 3/0091* (2013.01); *A61B 3/117* (2013.01); *A61B 3/14* (2013.01); *G02B 27/141* (2013.01); *G02B 27/0025* (2013.01)

(58) Field of Classification Search
USPC ........................................... 351/206
See application file for complete search history.

(56) References Cited

U.S. PATENT DOCUMENTS

| | | | |
|---|---|---|---|
| 4,820,037 A | 4/1989 | Kohayakawa et al. |
| 4,848,896 A | 7/1989 | Matsumoto |
| 4,952,049 A | 8/1990 | Matsumoto |
| 5,076,274 A | 12/1991 | Matsumoto |
| 5,233,372 A | 8/1993 | Matsumoto |
| 5,455,644 A | 10/1995 | Yazawa et al. |
| 5,615,278 A | 3/1997 | Matsumoto |
| 5,847,805 A | 12/1998 | Kohayakawa et al. |
| 6,158,864 A | 12/2000 | Masuda et al. |
| 6,273,565 B1 | 8/2001 | Matsumoto |

(Continued)

FOREIGN PATENT DOCUMENTS

JP    2007-296209 A    11/2007

*Primary Examiner* — Jack Dinh
(74) *Attorney, Agent, or Firm* — Fitzpatrick, Cella, Harper & Scinto

(57) ABSTRACT

Provided is an ophthalmologic apparatus including one dichroic mirror, which is arranged eccentrically with respect to an optical axis of light from an eye to be inspected to separate the light from the eye to be inspected; another dichroic mirror, which is configured to separate light separated by the one dichroic mirror by being transmitted through the one dichroic mirror; and a positive lens, which is configured to guide the light from the eye to be inspected to the one dichroic mirror as convergent light, and to guide the light from the eye to be inspected to the another dichroic mirror as divergent light, wherein an eccentric section of the one dichroic mirror and an eccentric section of the another dichroic mirror have a positional relationship of being substantially perpendicular to each other and having substantially the same eccentric amount, to thereby correct astigmatism.

19 Claims, 10 Drawing Sheets

(56) References Cited

U.S. PATENT DOCUMENTS

| | | |
|---|---|---|
| 6,327,375 B1 | 12/2001 | Matsumoto et al. |
| 6,456,787 B1 | 9/2002 | Matsumoto et al. |
| 6,488,377 B2 | 12/2002 | Matsumoto |
| 6,585,374 B2 | 7/2003 | Matsumoto |
| 6,779,890 B2 | 8/2004 | Matsumoto |
| 6,832,835 B2 | 12/2004 | Matsumoto |
| 7,500,754 B2 | 3/2009 | Yamaguchi et al. |
| 8,390,818 B2 | 3/2013 | Hirose et al. |
| 8,517,537 B2 | 8/2013 | Suehira et al. |
| 9,149,181 B2 | 10/2015 | Matsumoto et al. |
| 9,161,690 B2 | 10/2015 | Tomatsu et al. |
| 2007/0258045 A1 | 11/2007 | Yamaguchi et al. |
| 2012/0002166 A1 | 1/2012 | Tomatsu et al. |
| 2014/0104569 A1 | 4/2014 | Yamazaki |
| 2015/0042950 A1 | 2/2015 | Yamazaki |

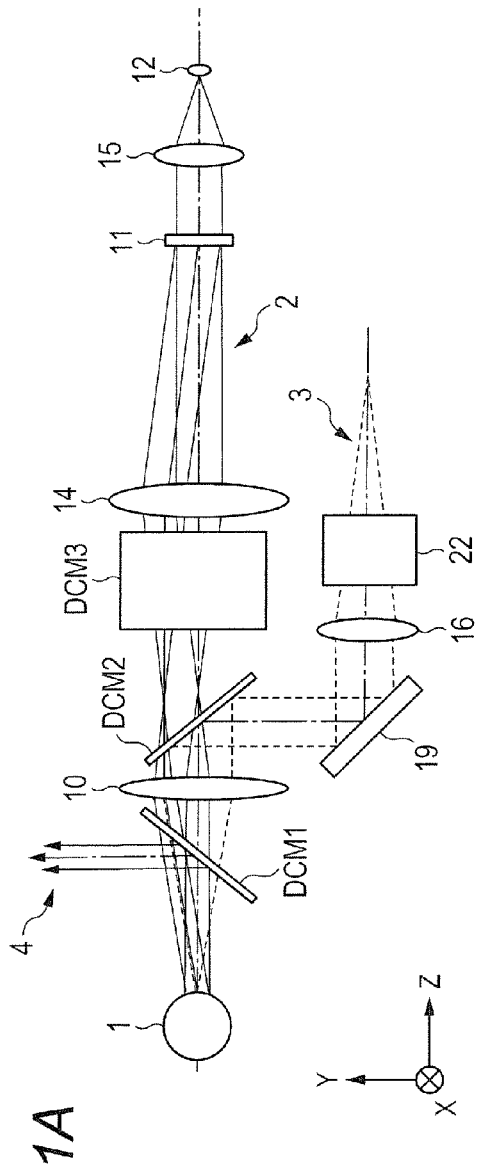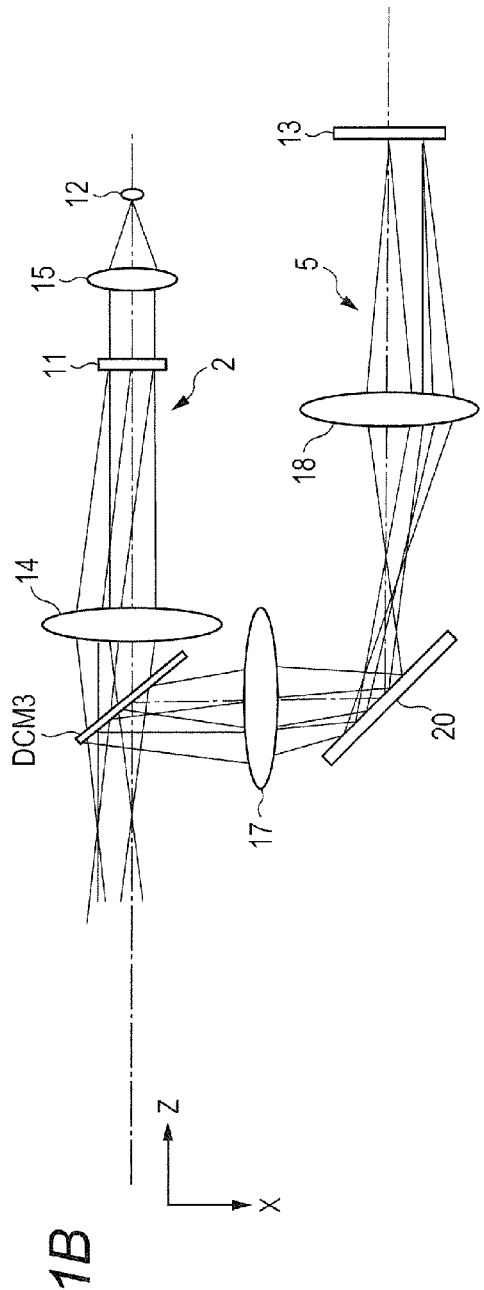
FIG. 1A
FIG. 1B

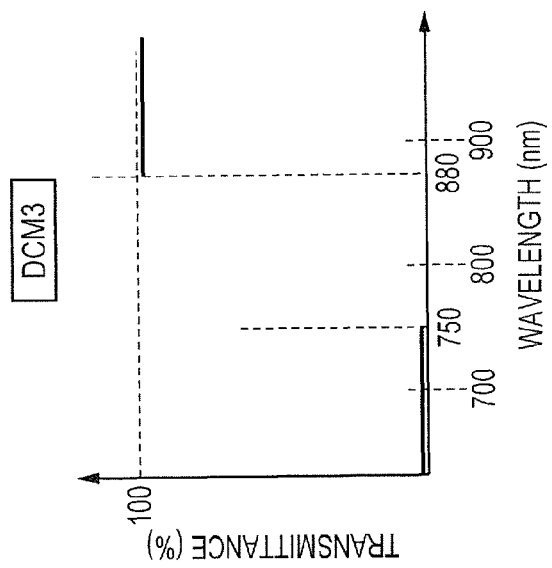
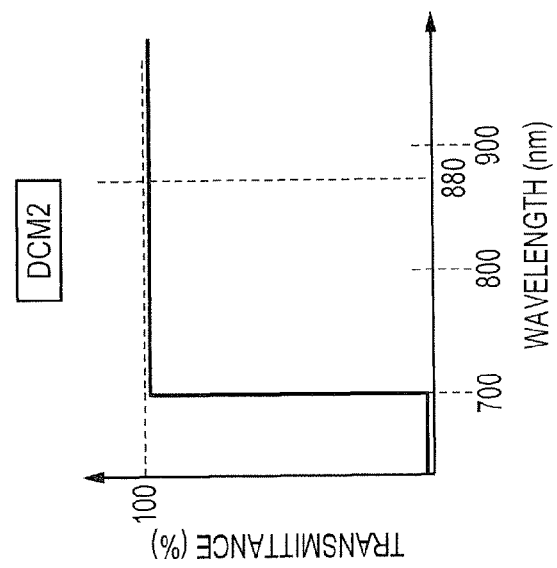
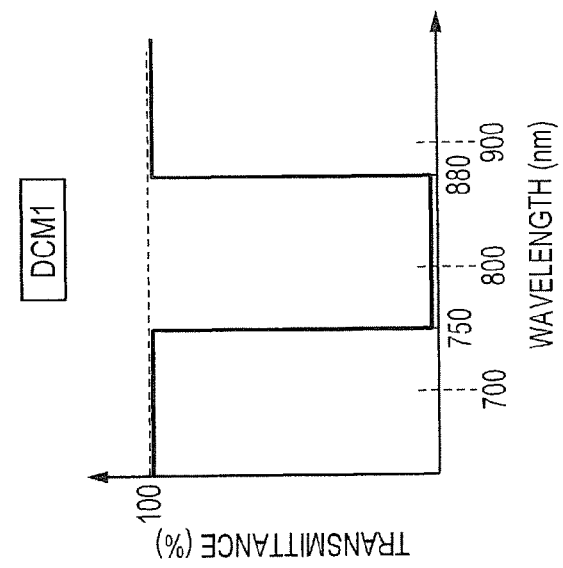

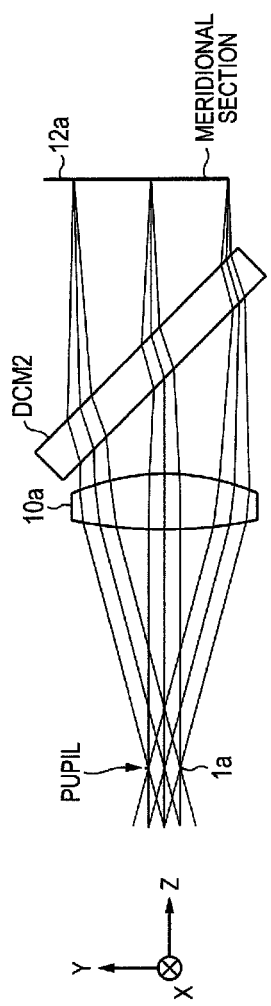

OPHTHALMOLOGIC APPARATUS

BACKGROUND OF THE INVENTION

Field of the Invention

The present invention relates to an inspection apparatus, exemplified by an ophthalmologic apparatus configured to inspect a fundus or an anterior segment of an eye to be inspected. The present invention relates to an apparatus in which a plurality of optical systems are arranged with use of beam splitters and which is configured to perform fundus photography and anterior segment photography, and more particularly, to an apparatus having a function of cancelling and correcting aberration of an eyeball of a subject to image a minute portion of a fundus with high magnification and high resolution.

Description of the Related Art

In recent years, a scanning laser ophthalmoscope (SLO) apparatus configured to two-dimensionally irradiate a fundus with laser light, receive light reflected from the fundus, and convert the received light into an image is known as an ophthalmologic image pickup apparatus that is one type of inspection apparatus. In particular, investigations have been made on an AO-SLO having an adaptive optics (AO) function for measuring aberration of the eye to correct the aberration when the fundus is imaged with high magnification. In this type of apparatus, a plurality of optical systems are arranged, such as a low-magnification wide-angle optical system configured to image the fundus with a wide angle of view, an AO optical system having the adaptive optics function and configured to image the fundus with high magnification and high resolution, an anterior segment optical system configured to image an anterior segment, and a fixation lamp indication optical system configured to change a fundus imaging range of the AO optical system. Optical paths of those optical systems are separated from one another as follows. Beam splitters, such as half mirrors and dichroic mirrors, are arranged so as to be eccentrically tilted, and the optical paths are separated from one another in a transmitting direction and in a reflecting direction.

In Japanese Patent Application Laid-Open No. 2007-296209, there is disclosed an AO-SLO apparatus in which optical paths are separated by beam splitters eccentrically tilted. This apparatus includes a plurality of beam splitters or dichroic mirrors. Note that, "eccentrically tilted" refers to the state in which an optical element such as a beam splitter is eccentrically arranged so that an optical axis thereof is tilted or rotated with respect to an optical axis of illumination light or the like. For example, one beam splitter separates a high-magnification fundus illumination system or a low-magnification fundus illumination system, which is configured to project illumination light to the fundus, from other optical systems. Further, another beam splitter separates a fixation indication optical system and an anterior segment observation optical system from other optical systems. A dichroic mirror separates a wavefront image sensor optical system, which is configured to measure aberration of the eye, from other optical systems. In Japanese Patent Application Laid-Open No. 2007-296209, there is also disclosed an aperture beam splitter configured to separate the low-magnification fundus imaging optical system and the high-magnification fundus imaging optical system from each other.

In an ophthalmologic apparatus such as the AO-SLO apparatus in which the plurality of optical systems are arranged as described above, the optical paths are separated by the eccentrically-tilted beam splitters as disclosed in Japanese Patent Application Laid-Open No. 2007-296209. However, those beam splitters are eccentrically tilted in the same plane (in the same drawing sheet), and hence axial astigmatism remains. Thus, for example, a problem such as distortion in an obtained image arises, and optical performance satisfactory for an image pickup apparatus cannot be obtained.

SUMMARY OF THE INVENTION

The present invention has been made in view of the above-mentioned circumstances, and provides an ophthalmologic apparatus having satisfactory optical performance, which is configured to perform fundus photography and anterior segment photography with use of beam splitters and a plurality of optical systems arranged therein.

According to one embodiment of the present invention, there is provided an ophthalmologic apparatus, including:
    four optical systems of a first optical system, a second optical system, a third optical system, and a fourth optical system;
    a first dichroic mirror, which is arranged eccentrically with respect to an optical axis of light from an eye to be inspected to separate the first optical system;
    a second dichroic mirror, to which the light from the eye to be inspected is guided through a positive lens, the second dichroic mirror being arranged eccentrically with respect to the optical axis of the light from the eye to be inspected to separate the third optical system; and
    a third dichroic mirror, which is arranged eccentrically with respect to the optical axis of the light from the eye to be inspected to separate the second optical system by reflection and to separate the fourth optical system by transmission,
    in which the positive lens is configured to cause light from a fundus of the eye to be inspected to enter the second dichroic mirror as convergent light, and to cause the light from the fundus of the eye to be inspected to enter the third dichroic mirror as divergent light, and
    in which an eccentric section of the second dichroic mirror and an eccentric section of the third dichroic mirror have a positional relationship of being perpendicular to each other and having substantially the same eccentric amount, to thereby correct astigmatism.

According to the one embodiment of the present invention, in the apparatus in which the plurality of optical systems are arranged and the optical paths thereof are separated from one another by the eccentrically-tilted dichroic mirrors, astigmatism to be generated may be satisfactorily corrected, and high optical performance may be obtained in any of the optical systems.

Further features of the present invention will become apparent from the following description of exemplary embodiments with reference to the attached drawings.

BRIEF DESCRIPTION OF THE DRAWINGS

FIGS. 1A and 1B are schematic configuration diagrams of primary optical elements in an AO-SLO apparatus according to a first embodiment of the present invention.

FIGS. 4A, 4B and 4C are graphs for showing characteristics of first, second, and third dichroic mirrors used in the second embodiment of the present invention, respectively.

FIG. 5 is an optical path diagram for illustrating axial center astigmatism generated by the second dichroic mirror.

DESCRIPTION OF THE EMBODIMENTS

Figure 2A:
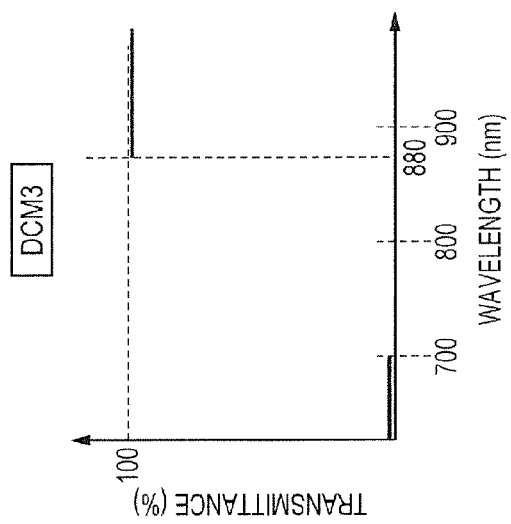
FIGS. 2A, 2B and 2C are graphs for showing characteristics of first, second, and third dichroic mirrors used in the first embodiment of the present invention, respectively.

Preferred embodiments of the present invention will now be described in detail in accordance with the accompanying drawings.

First Embodiment

Now, an embodiment of the present invention is described with reference to the accompanying drawings.

FIGS. 1A and 1B are schematic configuration diagrams of primary optical elements in an AO-SLO apparatus, which is an ophthalmologic apparatus according to a first embodiment of the present invention. FIG. 1A is an illustration of the configuration in a meridional section, and FIG. 1B is an illustration of the configuration in a sagittal section. In this apparatus, a fundus of an eye 1 to be inspected is two-dimensionally irradiated with light from a laser light source or a super luminescent diode (SLD) light source 12 through various kinds of optical systems and with use of a scanning scanner 11. Light reflected from the fundus after the irradiation returns through an optical path through which the light has passed from the light source to the fundus, and is received by a light receiving sensor 12. The received fundus-reflected light is converted into an image through photoelectric conversion processing or the like.

Note that, the scanning scanner 11 to be actually used is a reflective mirror device, but in FIGS. 1A and 1B, the scanning scanner 11 is illustrated as a transmissive scanner for the sake of convenience. Further, the light source 12 and the light receiving sensor 12 are illustrated as the same element, but the configuration actually arranged at the position indicated by reference numeral 12 is an end surface of an optical fiber, and an optical path for light emitted from the light source and an optical path for light received by the light receiving sensor are separated from each other by a fiber coupler (not shown) arranged behind the end surface of the optical fiber.

This apparatus includes an AO optical system 4 as a first optical system, an anterior segment optical system as a third optical system, a fixation lamp indication optical system 5 as a second optical system, and a low-magnification wide-angle optical system 2 as a fourth optical system. The AO optical system 4 has an adaptive optics (AO) function (not shown) for measuring aberration of the eye to cancel and correct the aberration, in order to have a wavefront correction function to image the fundus with high magnification and high resolution. An optical path of the AO optical system 4 is separated by a first dichroic mirror DCM1 arranged eccentrically with respect to the eye 1 to be inspected. An optical path of the anterior segment optical system 3 configured to image an anterior segment of the eye 1 to be inspected is separated by a second dichroic mirror DCM2. The second dichroic mirror DCM2 is arranged eccentrically with respect to the eye 1 to be inspected in order to separate light which has been reflected from the eye 1 to be inspected and passed through a positive lens 10 to be described later. In other words, the second dichroic mirror DCM2 is arranged so that an optical axis of the second dichroic mirror DCM2 is inclined with respect to an optical axis of light guided to the eye to be inspected 1. In the following, a description "arranged eccentrically" as used herein means that an optical element concerned is arranged so that an optical axis of the optical element is inclined with respect to an optical axis of measurement light or the like, which is the light guided to the eye 1 to be inspected. The fixation lamp indication optical system 5 displays an index for prompting fixation of the eye 1 to be inspected to change a fundus imaging range of the AO optical system 4. An optical path of the fixation lamp indication optical system is separated by a third dichroic mirror DCM3 by reflection. An optical path of the low-magnification wide-angle optical system 2 configured to image the fundus with a wide angle of view is separated by the third dichroic mirror DCM3 by transmission.

Note that, the positive lens 10 is arranged between the first dichroic mirror DCM1 and the second dichroic mirror DCM2. This arrangement of the positive lens 10 downsizes the optical systems behind the positive lens 10 (behind the second dichroic mirror DCM2) in the optical path of the positive lens 10. The positive lens 10 causes the light from the fundus of the eye 1 to be inspected to enter the second dichroic mirror DCM2 as convergent light, and causes the light from the fundus of the eye 1 to be inspected to enter the third dichroic mirror DCM3 as divergent light. The optical paths of those optical systems are separated from one another by the three first to third dichroic mirrors arranged to be eccentrically tilted so that the optical paths are transmitted through or reflected by the dichroic mirrors.

However, if convergent light or divergent light is caused to enter the dichroic mirror significantly eccentrically tilted, astigmatism is generated at the axial center.

FIG. 5 is an optical path diagram for illustrating the generation of axial center astigmatism due to the second dichroic mirror DCM2. In the apparatus according to this embodiment, a positive lens 10a (corresponding to the positive lens 10 of FIG. 1A) is arranged on the pupil side of the eye 1 to be inspected, and hence collimated light from a pupil 1a (light reflected from the fundus) is convergent light. This convergent light is transmitted through the second dichroic mirror DCM2, which is eccentrically tilted at 45 degrees in the meridional section (defining the YZ section), as convergent light, and forms an image on an imaging surface 12a arranged at a position corresponding to the light receiving sensor 12.

Figure 6:
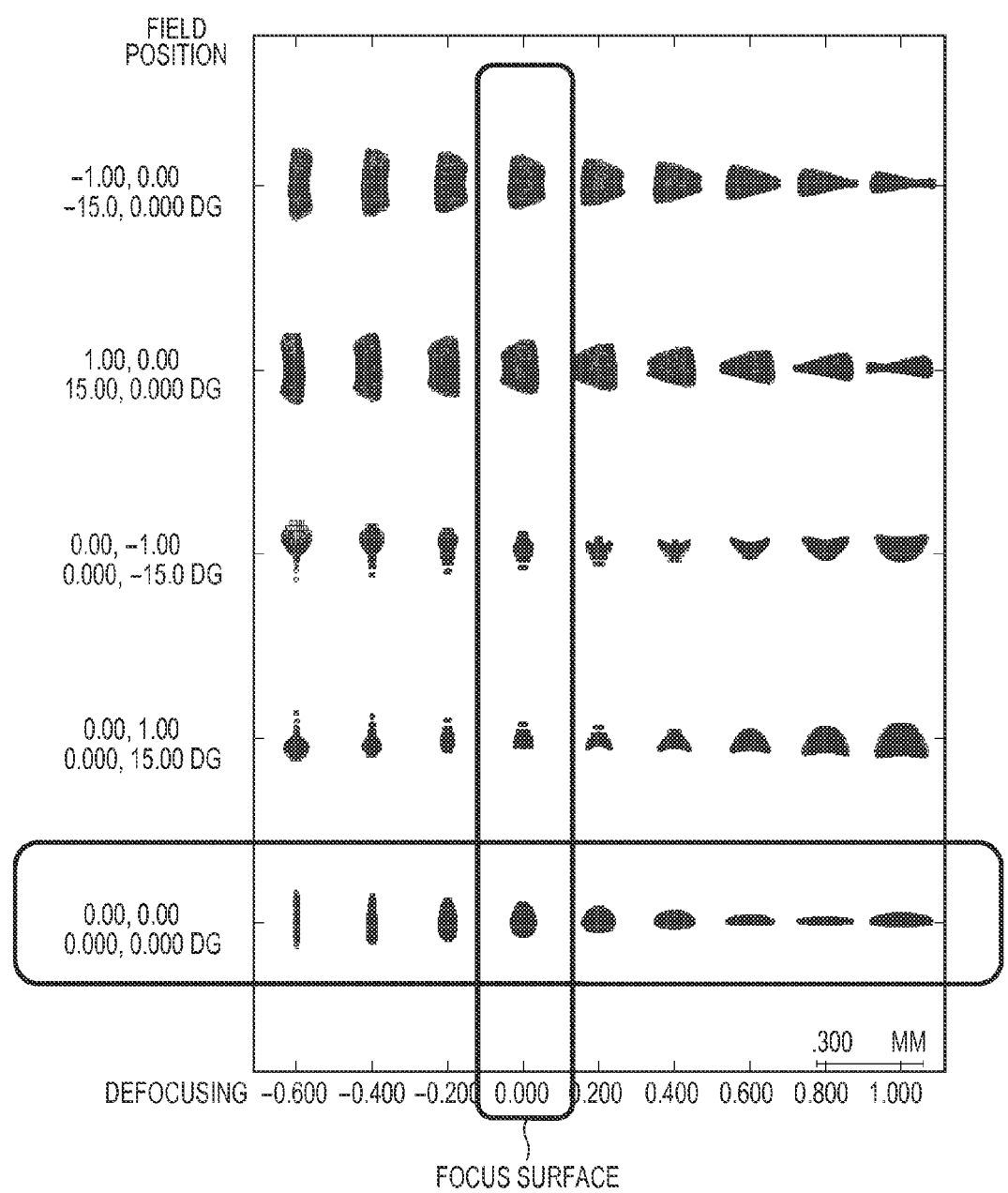
FIG. 6 is a spot diagram for showing spot image performance on an imaging surface affected by the axial center astigmatism generated by the second dichroic mirror.

FIG. 6 is a spot diagram for showing spot image performance on the imaging surface 12a. The horizontal axis indicates the defocus amount (mm) from a focus surface (imaging surface). The vertical axis indicates the angle of field, namely, a beam exit angle (X degrees, Y degrees) from the pupil center of the eye. The spot diagram shows the exit beams with Y of 0 degrees, +15 degrees, and −15 degrees in the meridional section and X of 0 degrees, +15 degrees, and −15 degrees in the sagittal section (XZ section) perpendicular to the meridional section. Note that, the beam with the exit angle (X degrees, Y degrees) of (0 degrees, 0 degrees) is an axial center flux. The spot diagram of the axial center flux changes from a vertically-long spot diagram to a horizontally-long spot diagram depending on the defocus amount, and large astigmatism is thus generated. Due to the astigmatism, the spot diagram on the focus surface is large and optical performance is poor.

Note that, in FIG. 5, the first dichroic mirror DCM1 as illustrated in FIG. 1A is not inserted between the pupil 1a of the eye and the positive lens 10a. The first dichroic mirror DCM1 is omitted because the light reflected from the fundus becomes collimated through the pupil of the eye and enters the first dichroic mirror DCM1 as collimated light, with the result that no astigmatism is generated.

Figure 7A:
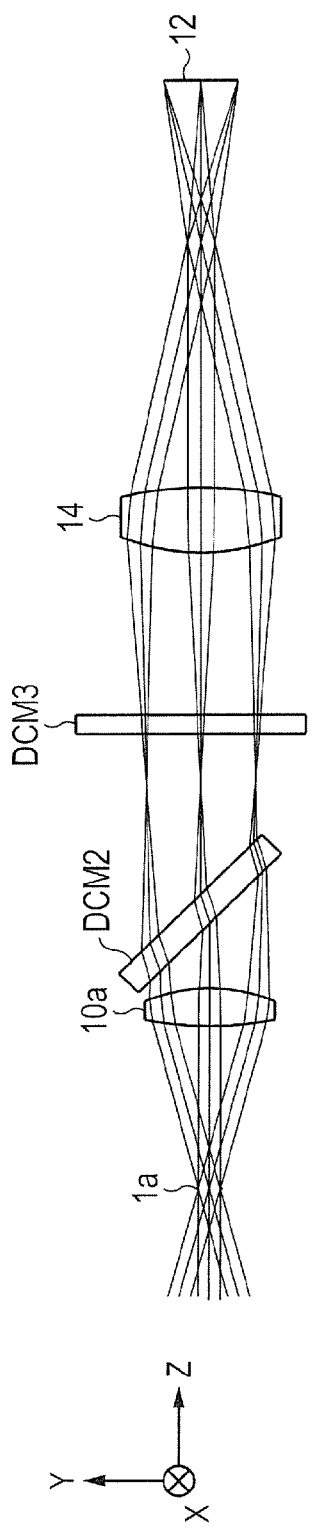
FIGS. 7A and 7B are optical path diagrams for illustrating how the astigmatism is corrected by using the third dichroic mirror according to the first embodiment of the present invention.
Figure 7B:
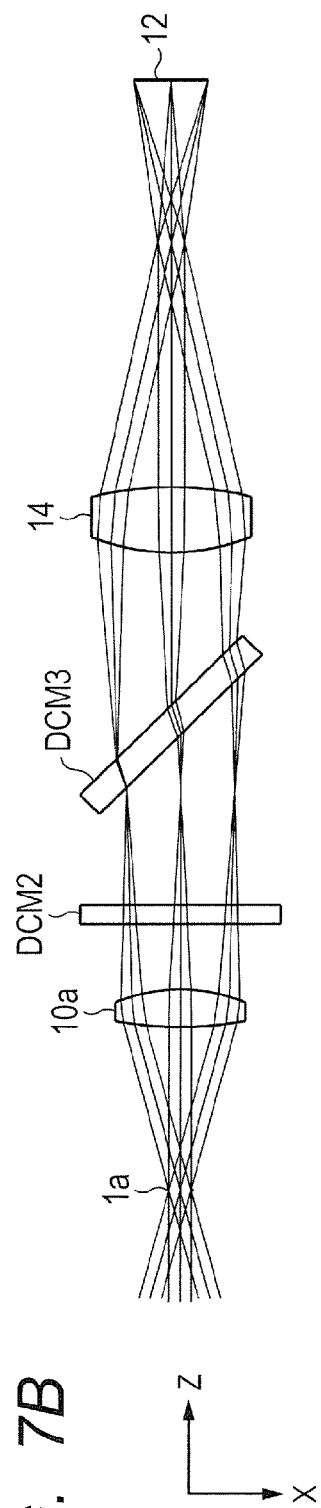

FIGS. 7A and 7B are optical path diagrams for illustrating a method of correcting the axial astigmatism according to the present invention. FIG. 7A is an illustration of arrangement of the configurations in the optical path in the meridional section (when viewed from the side), and FIG. 7B is an illustration of arrangement of the configurations in the optical path in the sagittal section (when viewed from above). The third dichroic mirror DCM3, a positive lens 14, and an ideal lens (not shown) are arranged behind the configurations illustrated in FIG. 5, to thereby form an image again. More specifically, divergent light that has passed through the second dichroic mirror DCM2 enters the third dichroic mirror DCM3. The entering light is not eccentrically tilted in the meridional section, but eccentrically tilted in the sagittal section perpendicular to the meridional section by an eccentric tilt amount of −45 degrees (the same amount as the eccentric tilt amount of the second dichroic mirror DCM2 in the meridional section). In this manner, the axial astigmatism is cancelled and corrected by the third dichroic mirror DCM3. In other words, astigmatism is generated by the third dichroic mirror DCM3 in a certain direction so as to cancel the astigmatism generated by the second dichroic mirror DCM2, with the result that astigmatism generated in the optical elements is suppressed as a whole. Further, in this embodiment, the positive lens 10a arranged between the pupil 1a of the eye and the second dichroic mirror DCM2 is an aspherical lens, to thereby also suppress aberration in a peripheral portion where the angle of view is large. Note that, in this embodiment, when the third dichroic mirror DCM3 is grasped as "another dichroic mirror" in the present invention, the second dichroic mirror DCM2 is grasped as "one dichroic mirror" in the present invention.

Figure 8:
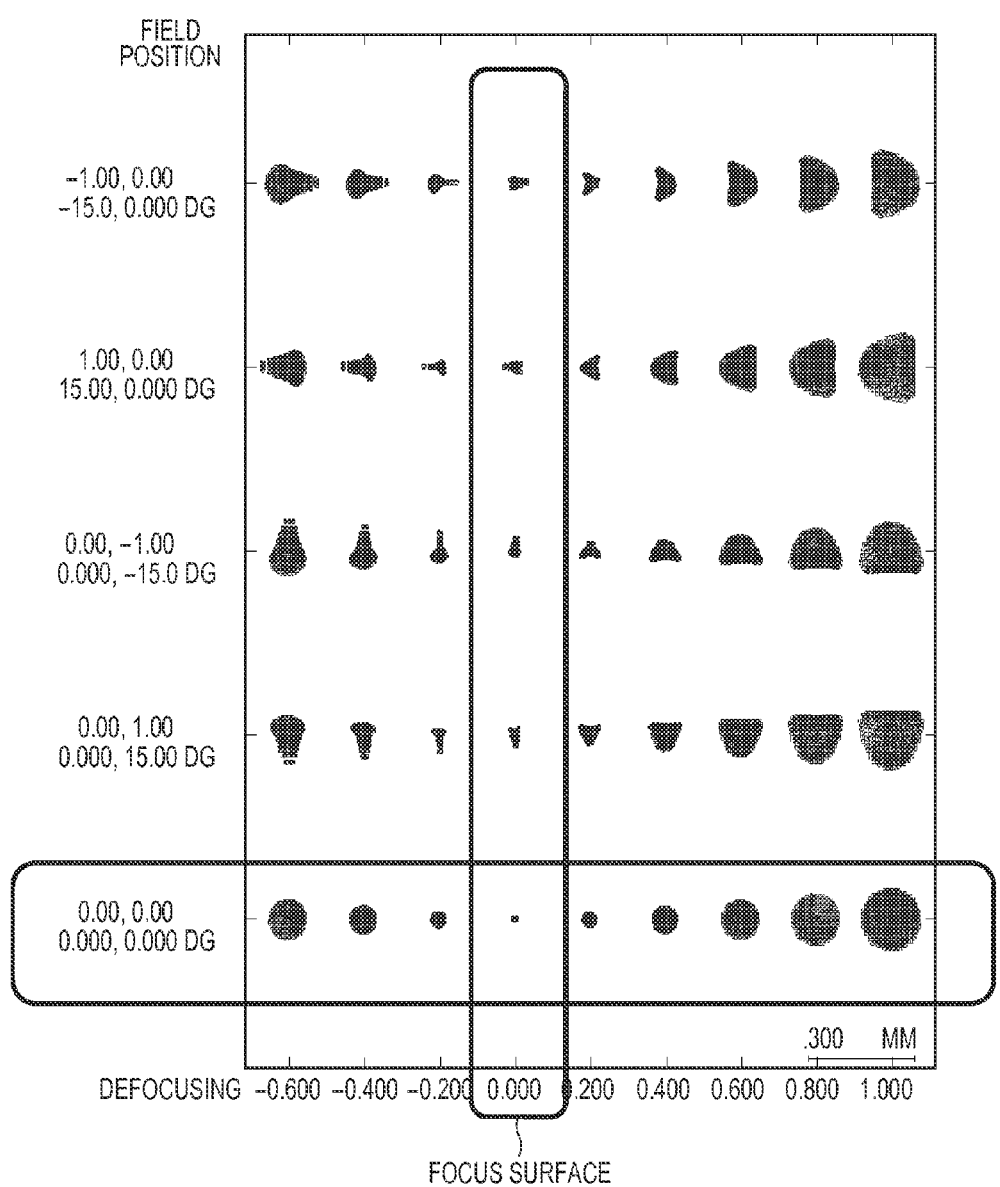
FIG. 8 is a spot diagram for showing spot image performance on the imaging surface obtained after the correction by the third dichroic mirror according to the first embodiment of the present invention.

Spot image performance in a spot diagram of FIG. 8 shows the suppressed aberration. In the spot diagram on the focus surface, both the axial aberration and the peripheral aberration are small, and satisfactory optical performance is obtained.

Figure 9:
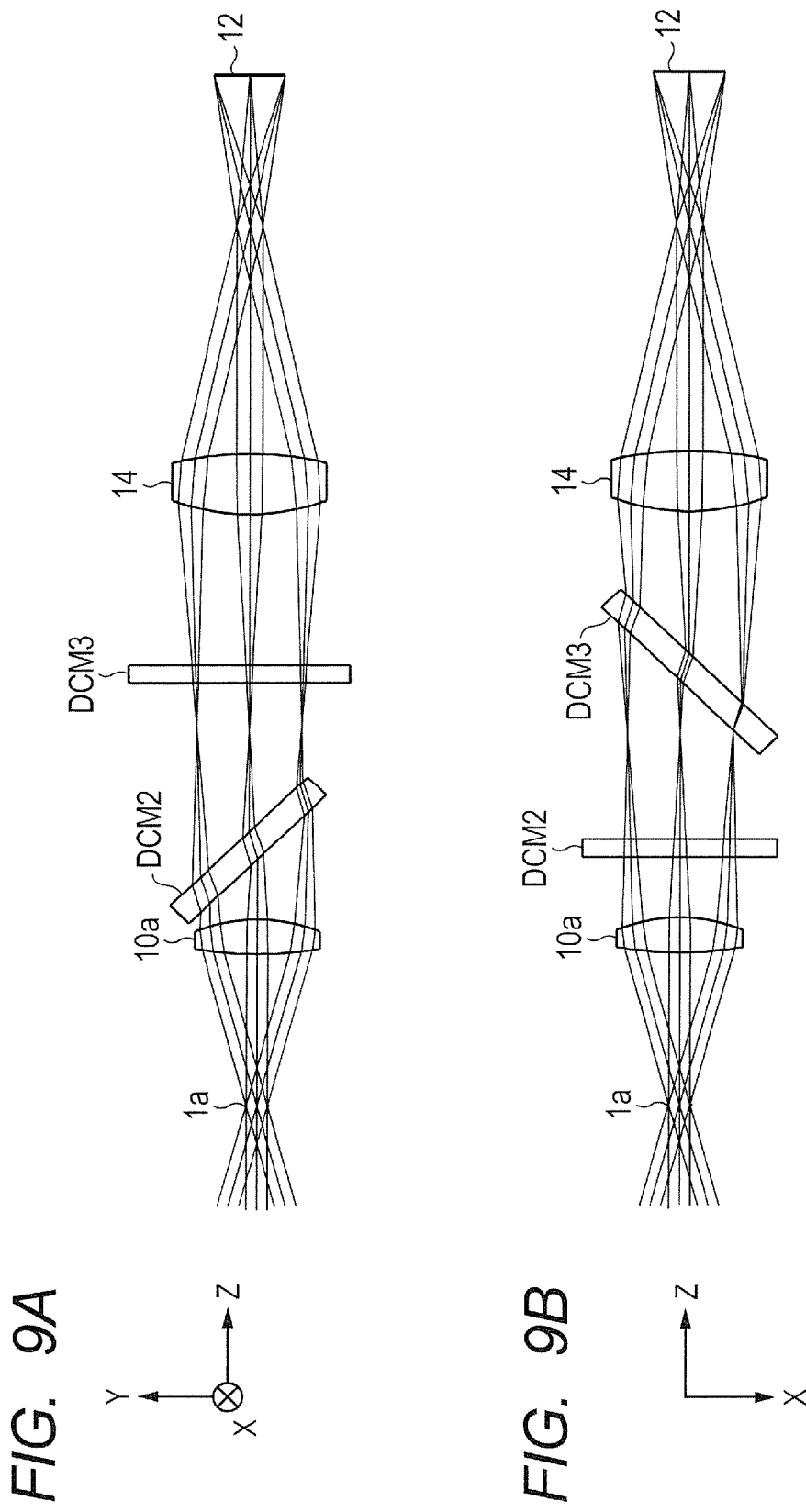
FIGS. 9A and 9B are optical path diagrams for illustrating another example of how the astigmatism is corrected by using the third dichroic mirror according to the first embodiment of the present invention.

In FIGS. 9A and 9B, another example of the astigmatism correcting configuration different from that illustrated in FIGS. 7A and 7B is exemplified. Each optical element illustrated in FIGS. 9A and 9B is basically the same as that illustrated in FIGS. 7A and 7B. In this example, however, the eccentric tilt amount of the third dichroic mirror DCM3 in the sagittal section is +45 degrees, which is opposite to that of the third dichroic mirror DCM3 of FIGS. 7A and 7B.

Figure 10:
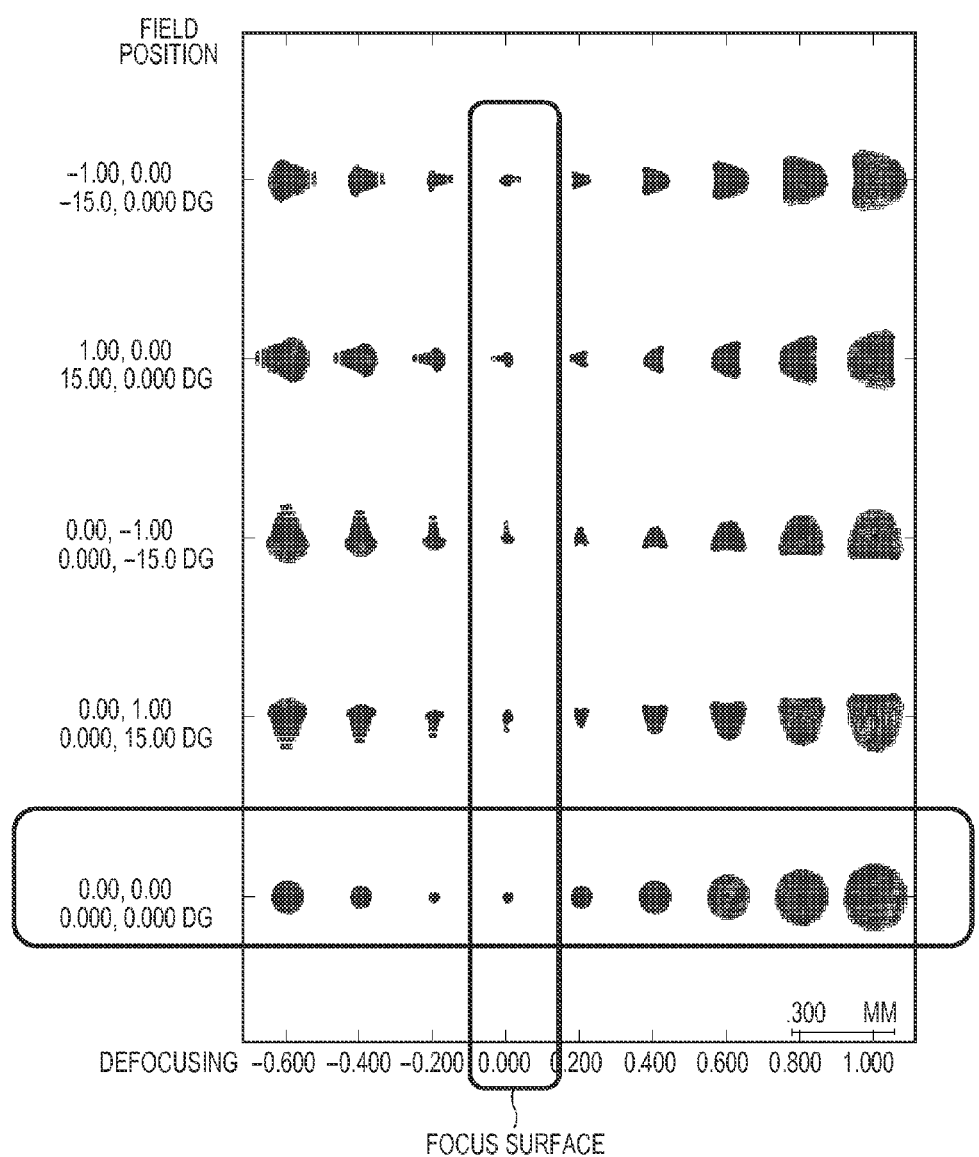
FIG. 10 is a spot diagram for showing spot image performance on the imaging surface obtained after another type of the correction by the third dichroic mirror according to the first embodiment of the present invention.

However, as understood from spot image performance shown in a spot diagram of FIG. 10, the configuration of FIGS. 9A and 9B obtains satisfactory optical performance comparable to that of the astigmatism correcting configuration exemplified in FIGS. 7A and 7B (spot image performance of FIG. 8) both for the axial aberration and the peripheral aberration.

As described above, the AO-SLO apparatus according to the first embodiment having the schematic configuration illustrated in FIGS. 1A and 1B includes the configuration illustrated in FIGS. 7A and 7B, that is, the third dichroic mirror DCM3 eccentrically tilted at −45 degrees in the sagittal section and the positive lens 10 having an aspherical surface. Then, an eccentric section of the second dichroic mirror DCM2 and an eccentric section of the third dichroic mirror DCM3 have a positional relationship of being perpendicular to each other and have substantially the same eccentric amount, to thereby correct the astigmatism. In this manner, the axial astigmatism and the peripheral aberration of the low-magnification wide-angle optical system 2 configured to image the fundus with a wide angle of view can be satisfactorily corrected. Note that, the eccentric section refers to a plane that is orthogonal to a plane including an optical axis of measurement light or the like and a tilt angle of an optical element arranged so that an optical axis of the optical element is tilted with respect to the optical axis of the measurement light. Further, the tilt angle of the optical element is referred to as "eccentric amount". Note that, in the present invention, it is preferred that the positional relationship of the eccentric sections and the like be grasped as being substantially perpendicular and having substantially the same eccentric amount. In this case, "being substantially perpendicular" and "having substantially the same eccentric amount" are the concept including not only "being completely perpendicular" and "having the same eccentric amount" but also "being substantially perpendicular" and "having substantially the same eccentric amount" that have an error small enough to reduce the astigmatism. Light that has passed through the third dichroic mirror DCM3 is collimated by the positive lens 14, and a two-dimensional light flux thereof is converted into a single light flux by the scanner (in an actual case, a reflective scanner) 11, and forms an image on the light receiving sensor 12 through a positive lens 15.

The anterior segment optical system 3, which has the optical path separated by the second dichroic mirror DCM2, is an optical system or an apparatus configured to form an image of light reflected from an eyeball surface (the pupil 1a of the eye 1 to be inspected), to thereby observe or image the state of the pupil plane of the eye 1 to be inspected. Divergent light from the eyeball surface (the pupil 1a of the eye 1 to be inspected) enters the first dichroic mirror DCM1 to be transmitted therethrough, is substantially collimated by the positive lens 10, and is reflected by the second dichroic mirror DCM2 so that the optical path of the anterior segment optical system 3 is separated. After the separation, the divergent light is reflected by a mirror 19, and then forms an image on a two-dimensional image pickup element (not shown) of a CCD or a CMOS through a lens 16. In this case, the light entering the first dichroic mirror DCM1 to be transmitted therethrough is divergent light to generate axial astigmatism, but the light reflected from the second dichroic mirror DCM2 is collimated light, and hence axial astigmatism is not generated. Therefore, a transmissive eccentric flat plate 22, which is eccentrically tilted at 45 degrees in the sagittal section (the same eccentric tilt amount as that of the first dichroic mirror DCM1, and may be −45 degrees instead), is interposed in an optical path behind the second dichroic mirror DCM2 through which the optical path of the anterior segment optical system 3 is separated and behind the lens 16 through which the light becomes convergent light.

In other words, the eccentric flat plate 22 is arranged in the optical system separated from the fourth optical system by any one of the third dichroic mirror DCM3 and the second dichroic mirror DCM2 as described later. Further, the second positive lens 16 is arranged in the same optical system. The second positive lens 16 causes the divergent light from the anterior segment of the eye 1 to be inspected, which has been transmitted through the first dichroic mirror DCM1 and collimated by the positive lens 10, to enter the eccentric flat plate 22 as convergent light. The eccentric flat plate 22 has the same amount of eccentricity as that of the eccentric section of the first dichroic mirror DCM1 in a section perpendicular to the eccentric section of the first dichroic mirror DCM1, and causes the convergent light to be transmitted therethrough, to thereby correct astigmatism generated by the first dichroic mirror DCM1. In other words, the eccentric flat plate 22 can correct the axial astigmatism generated by the anterior segment optical system 3, to thereby obtain satisfactory optical performance.

Next, in regard to the fixation lamp indication optical system 5, the relationship of convergent light and divergent light in the optical path diagram is exactly the same as that in the low-magnification wide-angle optical system 2 up to the third dichroic mirror DCM3. Note that, the fixation lamp indication optical system 5 is a display system, and hence the case of reverse beam tracing to a display device 13 is described. After the optical path is separated by the third dichroic mirror DCM3 by reflection, a reverse beam from the fundus is converted into convergent light by a lens 17. After that, the convergent light is further reflected by a mirror 20 to form an intermediate imaging surface, and then forms an image again by the lens 18. The display device 13 is arranged on this imaging surface. In this optical system, the axial astigmatism generated by the second dichroic mirror DCM2 due to the transmission of convergent light is cancelled by reflection of incident divergent light in a manner that the eccentric tilt amount of the third dichroic mirror DCM3 in the sagittal section is set to be the same as that of the second dichroic mirror DCM2. Note that, the configuration of suppressing the astigmatism by setting a predetermined eccentric tilt amount of the third dichroic mirror DCM3 in the sagittal section is the same as in the case of the low-magnification wide-angle optical system 2.

Figure 2B:
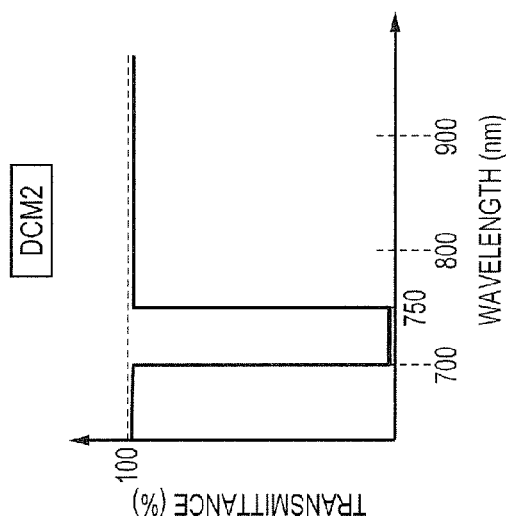
Figure 2C:
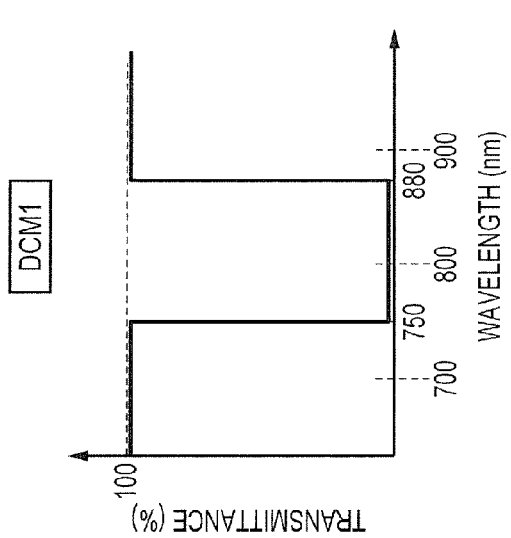

Further, in FIGS. 2A to 2C, spectral characteristics of the three dichroic mirrors DCM1, DCM2, and DCM3 used in the first embodiment (FIGS. 1A and 1B) of the present invention are shown. In FIGS. 2A to 2C, the horizontal axis indicates the wavelength (nm), and the vertical axis indicates the transmittance (%). The first dichroic mirror DCM1, which is configured to separate the optical path of the AO optical system 4, is desired to reflect light in wavelengths of from 750 nm to 880 nm and transmit light in the other wavelengths. The AO optical system 4 is required to have high resolving power, and hence the working wavelength of the AO optical system 4 is desired to be as short as possible in view of the ideal resolution. The short wavelength, however, leads to visible light. Thus, when the human eye is imaged, the subject feels dazzled so strongly that imaging cannot be performed for a long period of time. Accordingly, the wavelength range of from 750 nm to 880 nm, which is visible to the human eye but is sensed as weak light, is a balanced wavelength region.

The second dichroic mirror DCM2, which is configured to separate the optical path of the anterior segment optical system 3, has characteristics of reflecting light in wavelengths of from 700 nm to 750 nm and transmitting light in the other wavelengths. Many image pickup elements compatible with the wavelengths of from 700 nm to 750 nm are available at low cost, and hence the use of such inexpensive image pickup element can reduce the cost of the second dichroic mirror DCM2.

In regard to the third dichroic mirror DCM3, which is configured to separate the low-magnification wide-angle optical system 2 configured to image the fundus with a wide angle of view from the fixation lamp indication optical system 5, the low-magnification wide-angle optical system 2 is required to monitor the imaging for a long period of time, such as before and after the imaging by the AO optical system 4 and during the imaging of the anterior segment, and hence the low-magnification wide-angle optical system 2 is preferred to use a wavelength band of 880 nm or more, which is low in eye's luminosity function and invisible to the eye. Further, light in the fixation lamp indication optical system 5 has a visible wavelength. Therefore, the third dichroic mirror DCM3 is preferred to have characteristics of transmitting light in wavelengths of 880 nm or more and reflecting light in wavelengths of 700 nm or less.

Further, the focal length of the positive lens 10 is preferred to be 50 mm or more and 150 mm or less. When the focal length falls below the lower limit value, a sufficient distance (WD) cannot be secured between the first dichroic mirror DCM1 and the eyeball, and hence the human nose or the like may be brought into contact with the apparatus. On the other hand, when the focal length exceeds the upper limit value, the power of the positive lens 10 is too weak, and it becomes necessary to increase the optical systems arranged behind the positive lens 10.

As described above, the axial astigmatism, which is generated when the dichroic mirrors for optical path separation are eccentrically tilted so that transmissive convergent light or transmissive divergent light is caused to enter the dichroic mirrors, can be corrected through appropriate arrangement of the dichroic mirrors having the eccentric tilt amounts that can cancel out the axial astigmatism in the present invention. Consequently, satisfactory optical performance can be obtained in an AO-SLO apparatus.

Second Embodiment

Figure 3A:
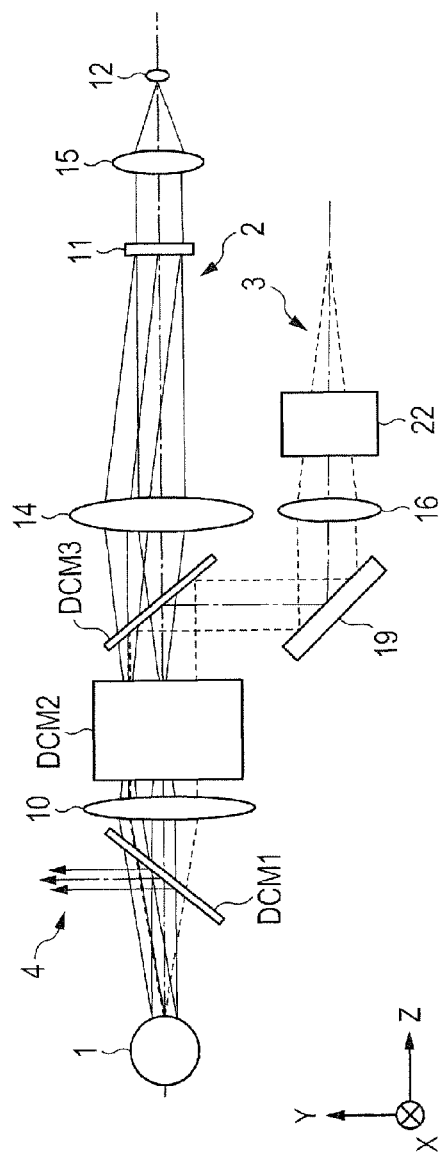
FIGS. 3A and 3B are schematic configuration diagrams of primary optical elements in an AO-SLO apparatus according to a second embodiment of the present invention.
Figure 3B:
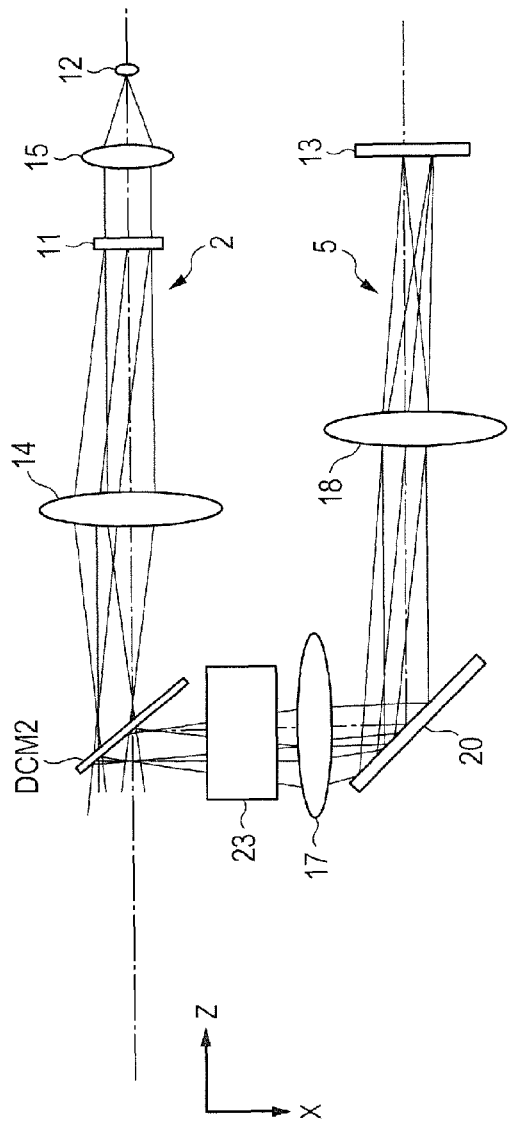

In regard to schematic configuration diagrams of primary optical elements in an AO-SLO apparatus according to a second embodiment of the present invention, FIG. 3A is an illustration of the configuration in the meridional section, and FIG. 3B is an illustration of the configuration in the sagittal section. Note that, in this embodiment, the configurations from the eye 1 to be inspected to the positive lens 10 are the same as those in the first embodiment of FIGS. 1A and 1B. Note that, in FIG. 3B, the illustration of the third dichroic mirror DCM3 is omitted for simplicity.

In this embodiment, in the low-magnification wide-angle optical system 2 configured to image the fundus with a wide angle of view, the second dichroic mirror DCM2 arranged behind the positive lens 10 is eccentrically tilted at −45 degrees in the sagittal section (XZ section). Similarly, the third dichroic mirror DCM3 is eccentrically tilted at 45 degrees in the meridional section (YZ section) perpendicular to the sagittal section. In this manner, the axial astigmatism is corrected similarly to the first embodiment. Note that, also in this embodiment, the positive lens 10 is an aspherical lens, and peripheral optical performance can be corrected as well. The configurations arranged behind the positive lens 14 are the same as those in the first embodiment, and descriptions thereof are herein omitted.

The optical path of the fixation lamp indication optical system 5 is separated by the second dichroic mirror DCM2 by reflection. Note that, also in this embodiment, the fixation lamp indication optical system 5 is a display system, and hence the case of reverse beam tracing to the display device 13 is described. After the optical path is separated by the third dichroic mirror DCM3 by reflection, the reverse beam from the fundus enters the second dichroic mirror DCM2 as convergent light to be reflected, and hence axial astigmatism is generated. Thus, an eccentric flat plate 23 eccentrically tilted at 45 degrees in the meridional section perpendicular to the sagittal section of the eccentric second dichroic mirror DCM2 is arranged behind the second dichroic mirror DCM2 to cause the divergent light to enter the second dichroic mirror DCM2 to be transmitted therethrough, to thereby cancel the axial astigmatism. After that, the reverse beam is collimated by the positive lens 17, is reflected by the mirror 20, and forms an image by the positive lens 18. The display device 13 is arranged on an imaging surface of the light.

The configuration of the anterior segment optical system 3 is the same as that of the low-magnification wide-angle optical system 2 up to the third dichroic mirror DCM3. Divergent light from the surface of the eye 1 to be inspected (the pupil of the eye) enters the first dichroic mirror DCM1 to be transmitted therethrough, and is substantially collimated by the positive lens 10. The collimated divergent light enters the second dichroic mirror DCM2 to be transmitted therethrough, and is reflected by the third dichroic mirror DCM3 to be separated from the low-magnification wide-angle optical system 2. Then, the light is reflected by the mirror 19, and then forms an image on a two-dimensional image pickup element (not shown) of a CCD or a CMOS through the lens 16. In this case, the light entering the first dichroic mirror DCM1 to be transmitted therethrough is divergent light, and hence axial astigmatism is generated. In contrast, the light entering the second dichroic mirror DCM2 to be transmitted therethrough and the light entering the third dichroic mirror DCM3 to be reflected thereby are collimated light, and hence axial astigmatism is not generated. Therefore, in this embodiment, the transmissive eccentric flat plate 22, which is eccentrically tilted at 45 degrees in the sagittal section, is interposed behind the third dichroic mirror DCM3 through which the optical path of the anterior segment optical system 3 is separated and behind the lens 16 through which the light becomes convergent light. Note that, the eccentric amount of the eccentric flat plate 22 is the same as the eccentric tilt amount of the first dichroic mirror DCM1. Further, the eccentric flat plate 22 may be tilted at −45 degrees similarly to the first embodiment. Through the insertion of the eccentric flat plate 22, the axial astigmatism generated by the first dichroic mirror DCM1 can be corrected, to thereby obtain satisfactory optical performance.

Further, in FIGS. 4A to 4C, spectral characteristics of the three dichroic mirrors DCM1, DCM2, and DCM3 used in the second embodiment (see FIGS. 3A and 3B) of the present invention are shown. The horizontal axis indicates the wavelength (nm), and the vertical axis indicates the transmittance (%). The first dichroic mirror DCM1, which is configured to separate the optical path of the AO optical system 4, is desired to reflect light in wavelengths of from 750 nm to 880 nm and transmit light in the other wavelengths (the same as in the first embodiment). The AO optical system 4 is required to have high resolving power, and hence the working wavelength of the AO optical system 4 is desired to be as short as possible in view of the ideal resolution. The short wavelength, however, leads to visible light. Thus, when the human eye is imaged, the subject feels dazzled so strongly that imaging cannot be performed for a long period of time. Accordingly, the wavelength range of from 750 nm to 880 nm, which is visible to the human eye but is sensed as weak light, is a balanced wavelength region. Next, the second dichroic mirror DCM2 configured to separate the fixation lamp indication optical system 5 has characteristics of reflecting light in wavelengths of 700 nm or less and transmitting light in the other wavelengths. The reason is that light used in the fixation lamp indication optical system 5 has a visible wavelength. The last third dichroic mirror DCM3 has characteristics of reflecting light in wavelengths of 750 nm or less and transmitting light in wavelengths of 880 nm or more. The optical path of light in wavelengths of 700 nm or less (fixation lamp indication optical system 5) has already been separated by the second dichroic mirror DCM2, and hence light reflected by the third dichroic mirror DCM3 has wavelengths of from 700 nm to 750 nm. Many image pickup elements compatible with the wavelength of from 700 nm to 750 nm are available at low cost, and hence the use of such inexpensive image pickup element can reduce the cost of the third dichroic mirror DCM3. Further, the low-magnification wide-angle optical system 2 is required to monitor the imaging for a long period of time, such as before and after the imaging by the AO optical system 4 and during the imaging of the anterior segment, and hence the low-magnification wide-angle optical system 2 is preferred to use light in a wavelength band of 880 nm or more, which is low in eye's luminosity function and invisible to the eye.

Further, the focal length of the positive lens 10 is preferred to be 50 mm or more and 150 mm or less. When the focal length falls below the lower limit value, a sufficient distance (WD) cannot be secured between the first dichroic mirror DCM1 and the eyeball, and hence the human nose or the like may be brought into contact with the apparatus. On the other hand, when the focal length exceeds the upper limit value, the power of the positive lens 10 is too weak, and it becomes necessary to increase the optical systems arranged behind the positive lens 10.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-182290, filed Sep. 8, 2014, which is hereby incorporated by reference wherein in its entirety.

What is claimed is:

1. An ophthalmologic apparatus, comprising:
   four optical systems of a first optical system, a second optical system, a third optical system, and a fourth optical system;
   a first dichroic mirror, which is arranged eccentrically with respect to an optical axis of light from an eye to be inspected to separate the first optical system;
   a second dichroic mirror, to which the light from the eye to be inspected is guided through a positive lens, the second dichroic mirror being arranged eccentrically with respect to the optical axis of the light from the eye to be inspected to separate the third optical system; and
   a third dichroic mirror, which is arranged eccentrically with respect to the optical axis of the light from the eye to be inspected to separate the second optical system by reflection and to separate the fourth optical system by transmission,
   wherein the positive lens is configured to cause light from a fundus of the eye to be inspected to enter the second dichroic mirror as convergent light, and to cause the light from the fundus of the eye to be inspected to enter the third dichroic mirror as divergent light, and
   wherein an eccentric section of the second dichroic mirror and an eccentric section of the third dichroic mirror have a positional relationship of being substantially perpendicular to each other and having substantially the same eccentric amount, to thereby correct astigmatism.

2. An ophthalmologic apparatus according to claim 1, further comprising a second positive lens and an eccentric flat plate that are arranged in an optical system separated from the fourth optical system by one of the second dichroic mirror and the third dichroic mirror,
   wherein the second positive lens is configured to cause divergent light from an anterior segment of the eye to be inspected, which is transmitted through the first dichroic mirror and collimated by the positive lens, to enter the eccentric flat plate as convergent light, and
   wherein the eccentric flat plate has the same eccentric amount as the eccentric amount of an eccentric section of the first dichroic mirror in a section perpendicular to the eccentric section of the first dichroic mirror, and is configured to cause the convergent light to be transmitted through the eccentric flat plate, to thereby correct astigmatism generated by the first dichroic mirror.

3. An ophthalmologic apparatus according to claim 2, wherein the convergent light transmitted through the eccentric flat plate is guided to the third optical system that is an optical system configured to observe the anterior segment of the eye to be inspected.

4. An ophthalmologic apparatus according to claim 3, wherein the second optical system comprises a fixation lamp indication optical system configured to display an index for prompting fixation of the eye to be inspected.

5. An ophthalmologic apparatus according to claim 3, wherein the third optical system comprises an optical system configured to image the anterior segment of the eye to be inspected.

6. An ophthalmologic apparatus according to claim 2,
   wherein the first optical system comprises an optical system having a wavefront correction function and configured to image the fundus with high magnification, and
   wherein the first dichroic mirror has characteristics of reflecting light in a wavelength range of from 750 nm to 880 nm and transmitting light in wavelengths outside the wavelength range.

7. An ophthalmologic apparatus according to claim 6, wherein the positive lens comprises an aspherical lens having a focal length of 50 mm or more and 150 mm or less.

8. An ophthalmologic apparatus according to claim 6, wherein the second optical system comprises a fixation lamp indication optical system configured to display an index for prompting fixation of the eye to be inspected.

9. An ophthalmologic apparatus according to claim 6, wherein the third optical system comprises an optical system configured to image the anterior segment of the eye to be inspected.

10. An ophthalmologic apparatus according to claim 2,
    wherein the fourth optical system comprises an optical system configured to image the fundus with a wide angle of view,
    wherein the fourth optical system is configured to image light in wavelengths of 880 nm or more, which is a longest wavelength among the four optical systems, and
    wherein the second dichroic mirror and the third dichroic mirror have characteristics of transmitting light in the wavelengths of 880 nm or more.

11. An ophthalmologic apparatus according to claim 10, wherein the positive lens comprises an aspherical lens having a focal length of 50 mm or more and 150 mm or less.

12. An ophthalmologic apparatus according to claim 11, wherein the second optical system comprises a fixation lamp indication optical system configured to display an index for prompting fixation of the eye to be inspected.

13. An ophthalmologic apparatus according to claim 11, wherein the third optical system comprises an optical system configured to image the anterior segment of the eye to be inspected.

14. An ophthalmologic apparatus according to claim 10, wherein the second optical system comprises a fixation lamp indication optical system configured to display an index for prompting fixation of the eye to be inspected.

15. An ophthalmologic apparatus according to claim 10, wherein the third optical system comprises an optical system configured to image the anterior segment of the eye to be inspected.

16. An ophthalmologic apparatus according to claim 2, wherein the second optical system comprises a fixation lamp indication optical system configured to display an index for prompting fixation of the eye to be inspected.

17. An ophthalmologic apparatus according to claim 2, wherein the third optical system comprises an optical system configured to image the anterior segment of the eye to be inspected.

18. An ophthalmologic apparatus according to claim 1, wherein the second optical system comprises a fixation lamp indication optical system configured to display an index for prompting fixation of the eye to be inspected.

19. An ophthalmologic apparatus according to claim 1, wherein the third optical system comprises an optical system configured to image an anterior segment of the eye to be inspected.

* * * * *